US010888319B2

(12) United States Patent
Vasta (10) Patent No.: US 10,888,319 B2
(45) Date of Patent: Jan. 12, 2021

(54) BONE STAPLE INSERTION TOOL AND RELATED METHOD

(71) Applicant: Gramercy Extremity Orthopedics LLC, Richardson, TX (US)

(72) Inventor: Paul J. Vasta, Richardson, TX (US)

(73) Assignee: GRAMERCY EXTREMITY ORTHOPEDICS LLC, Richardson, TX (US)

( * ) Notice: Subject to any disclaimer, the term of this patent is extended or adjusted under 35 U.S.C. 154(b) by 275 days.

(21) Appl. No.: 16/031,071

(22) Filed: Jul. 10, 2018

(65) Prior Publication Data

US 2019/0008514 A1    Jan. 10, 2019

Related U.S. Application Data

(60) Provisional application No. 62/530,823, filed on Jul. 10, 2017.

(51) Int. Cl.
| A61B 17/06 | (2006.01) |
| A61B 17/068 | (2006.01) |
| A61B 17/064 | (2006.01) |
| A61B 17/00 | (2006.01) |
| A61B 17/10 | (2006.01) |

(52) U.S. Cl.
CPC ...... *A61B 17/0682* (2013.01); *A61B 17/0642* (2013.01); *A61B 17/10* (2013.01); *A61B 2017/00367* (2013.01); *A61B 2017/00477* (2013.01); *A61B 2017/0645* (2013.01); *A61B 2017/0688* (2013.01)

(58) Field of Classification Search
CPC . A61B 17/068; A61B 17/064; A61B 17/0682; A61B 17/0642; A61B 17/072; A61B 17/88; A61B 17/8863
See application file for complete search history.

(56) References Cited

U.S. PATENT DOCUMENTS

| 8,137,351 B2 | 3/2012 | Prandi |
| 8,584,853 B2 | 11/2013 | Knight et al. |
| 9,095,338 B2 | 8/2015 | Taylor et al. |
| 9,855,036 B2 | 1/2018 | Palmer et al. |
| 9,861,357 B2 | 1/2018 | Palmer et al. |
| 9,931,115 B2 | 4/2018 | Morgan et al. |
| 10,010,320 B2 | 7/2018 | Wahl |
| 10,064,619 B2 | 9/2018 | Palmer et al. |

(Continued)

*Primary Examiner* — Christopher J Beccia
(74) *Attorney, Agent, or Firm* — Panitch Schwarze Belisario & Nadel LLP (57) ABSTRACT

A bone staple insertion tool for inserting a bone staple into a patient includes a body having a proximal portion, a distal surface and a fulcrum. The body defines a longitudinal axis and the fulcrum is positioned on the distal surface. The distal surface has a first end and a second end. A bone staple mount is fixed to the body and extends from the body proximate the first end. A force applicator is movably attached to the body. The force applicator has a gripping portion and a staple pin portion. The staple pin portion is positioned proximate the second end. The force applicator is configured to receive the bone staple. Upon actuation of the gripping portion, the staple pin portion bends the inter-axis of the bone staple across the fulcrum to an expanded state, wherein the first and second legs are positioned substantially parallel to the longitudinal axis.

24 Claims, 5 Drawing Sheets

(56) References Cited

U.S. PATENT DOCUMENTS

| | | | |
|---|---|---|---|
| 10,588,628 B2* | 3/2020 | Vasta | A61B 17/0682 |
| 2013/0206815 A1* | 8/2013 | Fox | A61B 17/0644 |
| | | | 227/176.1 |
| 2013/0213843 A1* | 8/2013 | Knight | A61L 2/26 |
| | | | 206/438 |
| 2016/0000434 A1* | 1/2016 | Cocaign | A61B 17/0684 |
| | | | 606/75 |
| 2016/0235460 A1* | 8/2016 | Wahl | A61B 17/0642 |
| 2017/0209142 A1 | 7/2017 | Wahl | |
| 2018/0271521 A1 | 9/2018 | Wahl | |
| 2018/0317910 A1 | 11/2018 | Wahl | |
| 2018/0344316 A1 | 12/2018 | Palmer et al. | |

* cited by examiner

BONE STAPLE INSERTION TOOL AND RELATED METHOD

CROSS-REFERENCE TO RELATED APPLICATIONS

The present application claims the benefit of U.S. Provisional Patent Application No. 62/530,823, filed on Jul. 10, 2017 and titled "Orthopedic Implant Insertion Tool and Method," the entire contents of which are incorporated herein by reference in its entirety.

BACKGROUND OF THE INVENTION

Surgical orthopedic bone staples are used in repairing fractured bone and/or bone that has undergone a surgical procedure for therapeutic purposes, e.g., deformity correction, reconstruction, arthrodesis, etc. Additionally, bone staples may be used to attached soft tissue, e.g., ligaments or tendons, to bone and may be used in conjunction with one or more fasteners, e.g., a bone plate and/or bone screws. Bone staples may be used to fuse bone in various anatomic locations of the human body such as bones of the foot, ankle, hand, and wrist, though the application is not limited to these areas. Their application is such that each leg of the staple is placed on an opposite side of the bone interface. In this light, the bone staples provide compression at the bone interface to promote fusion and allow surgeons to maintain bones in a desired anatomic position while attaching additional fixation means such as a bone plate or bone screws. Bone staples also may be utilized independently to fix or stabilize bones, or attach tissue to bone, and provide a low profile after implantation that is preferred where soft tissue coverage is limited such as in the extremities, for example the foot and hand.

Bone staples also provide a relatively simple and quick means of bone fixation and stabilization because of their relative ease of placement and thus removal after fusion takes place. Many bone staples are made of Nitinol and take advantage of the superelastic property of this material. The implant is formed with the legs in a compressed or inwardly biased state, which is expanded prior to implantation so that there is material bias to return to the compressed state to impart compression at the bone interface when implanted. Nitinol staples are designed and manufactured with specific dimensions and parameters, respectively, to provide specific compression forces. It is, therefore, desirable that the staples are delivered to the surgeon in a state that facilitates surgical application as well as optimal performance after implantation.

Traditionally, bone staples come in one of two forms. The first type are provided by the manufacturer in a non-sterilized form, which must be sterilized prior to use and then mounted to an insertion tool, which must also be sterilized, requiring multiple additional steps to be performed by the surgery team prior to use. The second type is generally provided by the manufacturer in a pre-sterilized form already mounted to a rigid insertion device and packaged in sterile packaging. However, such staples are pre-mounted in their expanded format or configuration. Where staples are supplied in the expanded format or configuration after days, weeks, or months of shipping, warehousing, and packaging in varying temperatures and conditions, the staple may be damaged or its elasticity may be reduced such that the staples is unable to return to its biased configuration to apply compression forces on the bone fragments or sections. Such tools, due to their fixed nature, also place additional forces on the staple and patient's bone when they are removed, thereby causing the possibility of transferring unwanted forces into a patient's newly repaired bones. Therefore, it would be advantageous to provide a pre-sterilized staple and insertion tool that can be delivered to surgeons in a non-expanded format. The preferred present invention addresses the above-described shortcomings of the prior art bone staples.

BRIEF SUMMARY OF THE INVENTION

In a first aspect the preferred present invention relates to a bone staple insertion tool having a body, a bone staple mount, and a force applicator having a gripping portion and a staple pin portion. The force applicator is configured to receive a bone staple and, upon actuation of the gripping portion, bend an inter-axis of the bone staple across a fulcrum located between the bone staple mount and the staple pin portion. The preferred bone staple insertion tool and bone staple are preferably supplied to the user in a sterilized packaging with the staple in an unexpanded configuration and is expanded prior to insertion by the user such that the staple is only in the expanded configuration for a relatively short amount of time immediately before insertion or implantation.

In another aspect of the preferred present invention relates to a method of inserting a bone staple into a patient with a bone staple insertion tool. The bone staple insertion tool has a body, a bone staple mount, a force applicator having a gripping portion and a staple pin portion, and a fulcrum disposed between the bone staple mount and the staple pin portion. In operation, the user removes the insertion tool and staple from the sterilized packaging and actuates the gripping portion to cause the bone staple to bend across the fulcrum. The staple is then inserted into the patient, particularly into the patient's bone, the gripping portion is de-actuated, and the bone staple insertion tool is rotated or pivoted relative to the staple to release the bone staple from the tool.

In yet another aspect, the preferred present invention is directed to a bone staple insertion tool for inserting a bone staple having an inter-axis and first and second legs into a patient. The insertion instrument or tool includes a body having a proximal portion, a distal surface and a fulcrum. The body defines a longitudinal axis and the fulcrum is positioned on the distal surface proximate the longitudinal axis. The distal surface has a first end and a second end. A bone staple mount is fixed to the body and extends from the body proximate the first end. A force applicator is movably attached to the body. The force applicator has a gripping portion and a staple pin portion. The staple pin portion is positioned proximate the second end. The force applicator is configured to receive the bone staple between the staple pin portion and the distal surface. After removal from the sterilized packaging and upon actuation of the gripping portion, the force applicator bends the inter-axis of the bone staple across the fulcrum located between the bone staple mount and the staple pin portion to move the bone staple to an expanded state. In the expanded state or configuration, the first and second legs of the bone staple are positioned substantially parallel to the longitudinal axis.

In a further aspect, the preferred present invention is directed to a method of inserting a bone staple into a patient with a bone staple insertion tool having a body with a fulcrum on a distal surface, a bone staple mount and a force applicator having a gripping portion and a staple pin portion, wherein the fulcrum is positioned on the distal surface between the bone staple mount and the staple pin portion. The method includes mounting the bone staple to a bone staple insertion tool with an inter-axis of the bone staple engaged by the gripping portion and the staple pin portion with a central portion of the inter-axis positioned on the fulcrum. The method also includes actuating the gripping portion, after removing the bone staple insertion tool from the sterilized packaging, to cause the staple pin portion to bend the inter-axis across the fulcrum such that first and second legs of the bone staple are substantially parallel to each other, inserting the bone staple into the patient, de-actuating the gripping portion, and rotating the bone staple insertion tool to release the bone staple from the tool.

The preferred present invention relates to an instrument to facilitate the implantation of a surgical orthopedic bone staple. An apparatus or insertion tool and method as herein described specifically relate to a device for securing and delivering a bone staple and inserting the bone staple into bone. The bone staple inserter comprises an elongate body dimensioned appropriately for the implantation of bone staples, with a proximal end and a distal end. The proximal end acts as a grip for holding the instrument and the distal end acts as a mount on which the bone staple is held for manipulation and implantation. The distal surface of the bone staple inserter also provides a fulcrum against which the bone staple is pressed in order to manipulate the staple into an expanded state where the bone staple legs are approximately parallel to each other. A force applicator is provided that comprises a proximal shaft, a pin that interfaces with the inserter handle and acts as a pivot, and a distal engagement pin that interfaces with the bone staple. The force applicator is configured to impart a rotational force against the bone staple in cooperation with the distal fulcrum of the inserter body to expand the staple in preparation for insertion after the insertion tool and staple are removed from a sterilized package.

In a preferred embodiment, the bone staple inserter is provided to the surgical theater in a terminally sterile package with the bone staple attached to the bone staple inserter. The bone staple is preferably configured such that it is mounted on the inserter in a relaxed, or unexpanded, state while in the sterilized package. A complimentary surgical kit for providing additional instruments is also offered in a separate terminally sterile package and contains additional surgical tools such as drill bits, staple sizing templates, drill guides, tamps, etc. Additionally, the bone staple, inserter, and additional surgical tools may be packaged together. During the surgical procedure, it is necessary for the surgeon to identify the correct size bone staple for the application and, therefore, a means for sizing the implant is preferred before selection and deployment of the terminally sterile packaged staple and inserter tool. It is therefore preferred to package the sizing tool in a separate container such that the correct size staple can be identified without sacrificing the sterility of the staple and the tool.

The preferred embodiment of the bone staple insertion instrument comprises a body for supporting a staple mount and a force applicator. The bone staple is preferably mounted to the bone staple insertion instrument in a sterilized package prior to use and for delivery to the user. The insertion instrument body includes a fulcrum projecting distally from the main distal aspect of the body. The fulcrum may be shaped as a double-sided ramp, rounded projection or other geometric shape suitable for the purpose of a fulcrum. The staple mount is attached to the distal aspect of the insertion instrument body located at a distance from the fulcrum appropriate for the staple size to be utilized with the insertion tool. The position of the staple mount is determined such that the bottom surface of the staple is held against the mount proximate to the bend between the intersection of a first leg and the inter-axis and the top surface of the staple is held against the insertion instrument body with the mid-point of the staple inter-axis approximately located at the apex of the fulcrum. The force applicator is pivotally mounted to the insertion instrument body such that the force applicator may rotate about the pivot point. A bone staple positioner is located at the distal end of the force applicator such that the staple is held against the positioner proximate to the bend between the intersection of a second leg and the inter-axis. The force applicator has an elongate handle extending from the pivot to the proximal end such that the length of the elongate handle is substantially longer than the length of the force applicator between the pivot and the distal positioner. In a first position, the force applicator positioner is engaged with the staple such that the staple is held in a non-expanded state or configuration against the insertion instrument body in a secure manner. In a second position, the force applicator has been rotated about the pivot point by applying a force against proximal elongate handle in a manner causing the distal positioner to translate the applied force against the bone staple and creating a bending moment within the inter-axis in relation to the fulcrum. The bone staple inter-axis is caused to mechanically react to the bending moment, being held in place by the mount, by bending at the point of the fulcrum, thereby positioning the first and second staple legs to be oriented in a parallel relationship with the force applicator in the second position.

In another exemplary embodiment, a second staple mount is attached to the distal aspect of the insertion instrument body located at a distance approximately equal to the distance from the first staple mount to the fulcrum. The second staple mount is attached to the body and communicates slidably within a hole through the body. The distal end of the force applicator is attached to the second mount, thereby transferring the rotational force imparted by the force applicator rotating from the first position to the second position onto the second mount in a direction from distal to proximal. The translational force is thereby imparted onto the second mount causing the second mount to translate the applied force against the bone staple creating a bending moment within the inter-axis in relation to the fulcrum. The bone staple inter-axis is caused to mechanically react to the bending moment, being held in place by the first mount, by bending at the point of the fulcrum and thereby positioning the first and second staple legs to be oriented in a substantially parallel relationship with the force applicator in the second position.

In another embodiment, the proximal end of the second staple mount is threadably engaged with a proximal thumb wheel or other rotatable member located in abutment against the insertion instrument body proximal to the fulcrum. Rotation of the rotatable member causes the threaded mount to translate proximally at a rate determined by the pitch of the threads. The translation of the threaded mount induces a force against the bone staple creating a bending moment within the inter-axis in relation to the fulcrum as previously described.

In another embodiment, the force applicator is engageable with the insertion instrument body such that the force applicator may be temporarily locked in position one, position two, or any other position appropriate for the function of the insertion instrument. The force applicator may be packaged and distributed while locked in position one, wherein the one staple is in a relaxed position or configuration, such that the bone staple is retained in position against the first mount and the fulcrum, thereby effectively enabled to be utilized when deployed at the surgical site. When the implant site is prepared and the surgeon is ready to implant the bone staple, the insertion tool and bone staple are removed from the sterilized package, the force applicator can be moved to, and temporarily locked at, position two, wherein the bone staple is in the expanded position or configuration. The locking means may be of those known such as a mechanical catch or lever.

In yet another embodiment, the bone staple insertion instrument is packaged with the staple positioned in engagement with the first mount in a sterilized package, the force applicator or second mount, and the fulcrum. Preferably, the force applicator is in the first position whereby the staple is held securely by the insertion instrument but not in an expanded position, i.e., with the staple legs approximately in the initial manufactured orientation with respect to each other or tapering toward each other and the inter-axis substantially straight or in its initial manufactured orientation. The staple and insertion instrument together are packaged in a terminally sterile container independently from additional instruments or implants.

In yet another embodiment, a method of using the insertion instrument for implanting a bone staple in a surgical site of a patient includes mounting a bone staple onto the distal aspect of the insertion instrument such that the staple is in contact with the first mount, the force applicator or second mount, and the fulcrum; positioning the insertion instrument and mounted bone staple in a sterilized package; removing the insertion instrument and bone staple from the package prior to use; rotating the force applicator to the first position whereby the staple is held securely on the insertion instrument but not expanded; expanding the bone staple by rotating the force applicator to the second position thereby orienting the first and second legs of the staple in a parallel relationship; inserting the bone staple into parallel-drilled holes in a bone of a patent; rotating the force applicator in a direction toward the first position thereby releasing the force on the staple whereby the staple bias will compress the bone between the legs; disengaging the insertion instrument from the bone staple; forcing the staple inter-axis bottom surface toward the bone surface by pressing or tamping the top surface of the inter-axis; and closing the incision.

In an additional exemplary embodiment, rotating the force applicator from the first position to the second position comprises forcing the proximal elongated portion of the force applicator toward the proximal elongated portion of the insertion instrument body and using the instrument body to counteract the force applied to the force applicator. Temporarily locking the force applicator in the first or second position comprises engaging a mechanical lock mechanism whereby further rotation of the force applicator is restricted. Unlocking the force applicator comprises disengaging a mechanical lock mechanism whereby further rotation of the force applicator is allowed. Disengaging the insertion instrument from the staple comprises rotation of the insertion instrument about its long axis or longitudinal axis relative to the staple whereby the staple mount and the distal portion of the force applicator or second staple mount becomes clear of the staple inter-axis. The insertion instrument may then be removed from the incision site. It is also contemplated that the proximal end of the insertion instrument be configured to interface with the proximal aspect of the bone staple for the purpose of tamping the staple into the bone, thus eliminating the need for a separate tamping instrument.

In yet another exemplary embodiment, the bone staple insertion instrument body may be made from various materials including metal, polymeric materials and plastic or nearly any structural material that is able to take on the general size and shape of the body, withstand the normal operating conditions of the body and perform the preferred functions of the body. To accommodate a plurality of staple sizes, i.e., having varied inter-axis lengths, the attachment locations of the first mount and force applicator, or second mount as applicable, on the insertion instrument body preferably varies such that the bone staple is held both in relaxed and expanded states with the center of the inter-axis proximate to the fulcrum at the distal end of the body. To gain manufacturing and production efficiencies, it would be beneficial to limit the number of uniquely dimensioned components making up each insertion instrument. That is, it would be desirable to have a body design to accommodate a plurality of staple sizes. Additionally, it would be desirable for a mount design and a force applicator design to accommodate a plurality of staple sizes. In an exemplary embodiment, the insertion instrument body includes two bore holes to accommodate the pin of a force applicator, a first bore hole to be associated with the force applicator mounted on a first body side to accommodate a first bone staple inter-axis length, and a second bore hole to be associated with the force applicator mounted on a second body side to accommodate a second bone staple inter-axis length. The insertion instrument body also includes two bore holes to accommodate the bone staple mount, a first bore hole to be associated with the bone staple mount incorporated into the distal end of the insertion instrument body at a first location to accommodate a first bone staple inter-axis length, and a second bore hole to be associated with the bone staple mount incorporated into the distal end of the insertion instrument body at a second location to accommodate a second bone staple inter-axis length.

BRIEF DESCRIPTION OF THE SEVERAL VIEWS OF THE DRAWINGS

The foregoing summary, as well as the following detailed description of preferred embodiments of the instrument or tool, implant and method of the present application, will be better understood when read in conjunction with the appended drawings. For the purposes of illustrating the bone staple insertion tool, there are shown in the drawings preferred embodiments. It should be understood, however, that the application is not limited to the precise arrangements and instrumentalities shown. In the drawings.

DETAILED DESCRIPTION OF THE INVENTION

Certain terminology is used in the following description for convenience only and is not limiting. Unless specifically set forth herein, the terms "a", "an" and "the" are not limited to one element but instead should be read as meaning "at least one." The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred bone staple insertion tool or instrument and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component, insertion tool or related feature of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The present disclosure describes an apparatus and method for preferred embodiments of a bone staple insertion tool or instrument, generally designated 100, 300, 400, 500. Referring to FIGS. 1-8, the bone staple insertion instrument or tool 100, 300, 400, 500 comprises a body 110, 310, 410, 510 with a proximal elongate handle for gripping and manipulating the instrument or tool 100, 300, 400, 500 and a distal bone staple support surface and fulcrum 170, 370, 470, 570, a force applicator comprised of a proximal elongate lever arm in the first, second and fourth preferred embodiments, a pivot pin oriented substantially orthogonal to a longitudinal axis 110b, 310b, 510b of the instrument or tool 100, 300, 500 in the first, second and fourth preferred embodiments, a force application pin, and a bone staple mount. In the preferred embodiments, the force applicator 120, 320, 420, 520 acts directly on a bone staple 190 to securely retain and expand the bone staple 190 for handling and surgical implantation, respectively. In the preferred embodiments, the force applicator acts directly on the bone staple mount, and in the third preferred embodiment, the force applicator 420 is configured as a threaded nut 430 acting on a second bone staple mount. It is contemplated that the configuration of the preferred embodiments presented in this disclosure may be applied to other orthopedic implants for retention and/or implantation, including bone plates that may require bending which can be achieved in similar fashion to the force applicator acting on the bone staple to expand the bone staple or bone plate by bending the inter-axis of the bone staple or the bone plate across a fulcrum.

FIGS. 1-4b illustrate the bone staple insertion tool or instrument 100 of the first preferred embodiment. The first preferred insertion tool or instrument 100 is configured for inserting a bone staple 190 having an inter-axis 200 and first and second legs 210, 220 into a patient to apply a joining force to bone segments or attach soft tissue to the bone. The first preferred bone staple insertion tool or instrument 100 includes the body 110, a force applicator 120 and a bone staple mount 180. The body 110 includes a proximal portion 110a, a distal surface 111 and a fulcrum 170. The body 110 defines a longitudinal axis 110b and the fulcrum 170 is positioned on the distal surface 111 proximate the longitudinal axis 110b. The distal surface 111 has a first end 111a and a second end 111b. A bone staple mount 180 is fixed to the body 110 and extends from the body 110 proximate the first end 111a. The force applicator 120 is movably attached to the body 110 and has a proximal gripping portion 150 and a staple pin portion 140, preferably at a distal end. The staple pin portion 140 is positioned proximate the second end 111b in an assembled configuration. The force applicator 120 is configured to receive the bone staple 190 between the staple pin portion 140 and the distal surface 111 and, upon actuation of the gripping portion 150, bend the inter-axis 200 of the bone staple 190 across the fulcrum 170. Bending the bone staple 190 from an unexpanded position or configuration to an expanded position or configuration urges the first and second legs 210, 220 into a position substantially parallel to each other in the expanded configuration for insertion into the patient. The first and second legs 210, 220 are also preferably positioned substantially parallel to a longitudinal axis 110b of the body 110 in the expanded configuration. The proximal portion 110a of the body 110 may be used to manipulate the tool or instrument 100 during use, such as for inserting the staple 190 into the patient and for pivoting the tool or instrument 100 relative to the patient and bone staple 190 following insertion.

Figure 1:
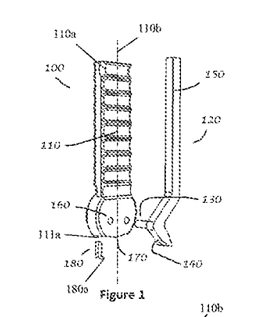
FIG. 1 is a front perspective, exploded view of a bone staple insertion tool or instrument in accordance with a first preferred embodiment of the present invention.
Figure 2:
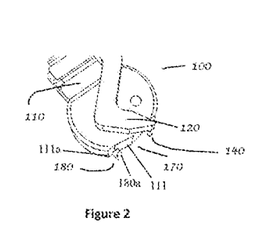
FIG. 2 is a front perspective, magnified view of a distal end of the bone staple insertion tool or instrument of FIG. 1 in a non-expanded or relaxed state or configuration.

Referring specifically to FIG. 1, an exploded view demonstrates the location of a pivot pin 130 of the force applicator 120 and an associated pivot hole 160 located in the body 110. The force applicator pivot pin 130 is preferably rotatably engaged in the pivot hole 160 such that the force applicator 120 is able to rotate about the axis of the pivot pin 130 relative to the insertion instrument body 110. The force applicator 120 includes a gripping portion 150 proximal to the pivot pin 130 and a staple pin portion 140 distal to the pivot pin 130. The staple pin portion 140 is preferably movably positioned proximate the second end 111b of the distal surface 111 in the assembled configuration to engage the bone staple 190 near an intersection of the second leg 220 and the inter-axis 200 in the non-expanded or relaxed state or configuration (FIG. 3a) and the expanded state or configuration (FIG. 3b). A bone staple mount 180 is fixed at the most distal aspect of body 110 such that the distal end of the bone staple mount 180 extends from the distal end of the body 110 or from the distal surface 111, as shown in FIG. 2. The bone staple mount 180 includes a first pin 180a that extends substantially perpendicular to the longitudinal axis 110b beneath the distal surface 111 to define a first space into which the inter-axis 200 of the bone staple 190 may be inserted, preferably near an intersection of the first leg 210 and the inter-axis 200. The bone staple fulcrum 170 is located at the most distal aspect of the body 110 on the distal surface 111 between the bone staple mount 180 and the staple pin portion 140 in the assembled configuration such that the distal surface 111 of the body 110 extending outward in either direction from the fulcrum 170 is proximal to the fulcrum 170. The distal surface 111, specifically, tapers from the fulcrum 170 proximally toward both the first end 111a and the second end 111b such that the fulcrum 170 is the most distal portion of the body 110. In the first preferred embodiment, the distal surface 111 linearly tapers proximally with increasing distance outward from the fulcrum 170, however, alternative embodiments may utilize other geometries, such as a step or curve. The distal surface 111, specifically, tapers away from the body 110 from opposing outward or distal ends toward the fulcrum 170, such that the fulcrum 170 is the most distally positioned portion of the distal surface 111. The bone staple tool 100 with the bone staple 190 mounted thereto is preferably positioned in the non-expanded configuration, sterilized and positioned in a sterilized package for delivery to a user.

In the first preferred embodiment, the bone staple mount 180 with the first pin 180a is substantially L-shaped and the staple pin portion 140 is also substantially L-shaped, particularly at their distal ends. The staple pin portion 140 preferably includes a second pin 140a that extends below the distal surface 111 in the assembled configuration to define an insertion space into which the inter-axis 200 is inserted in the working configuration. The first and second pins 180a, 140a preferably extend in opposite directions or are oriented in generally opposing directions relative to the body 110 such that the body 110 may be twisted or pivoted following insertion of the bone staple 190 to disengage or release the bone staple 190 from the instrument or tool 100. In the first preferred embodiment, the body 110, force applicator 120 and the bone staple mount 180 are constructed of a biocompatible polymeric or metallic material, but are not so limited. The body 110, force applicator 120 and bone staple mount 180 may be constructed of nearly any rigid, structural material that is able to take on the general size and shape of the described components, withstand the normal operating conditions of the components and perform the preferred functions of the components, as is described herein.

Figure 3A:
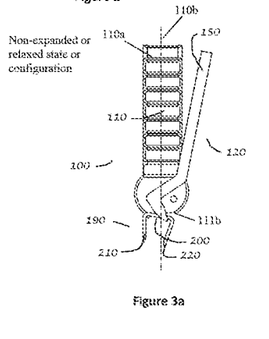
FIG. 3a is a front elevational view of the bone staple insertion tool or instrument of FIG. 1 with a bone staple mounted thereon in the non-expanded or relaxed state or configuration.
Figure 3B:
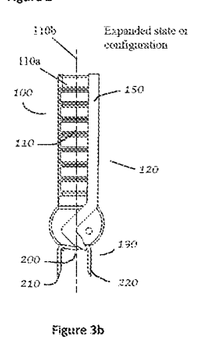
FIG. 3b is a front elevational view of the bone staple insertion tool or instrument of FIG. 1 with a bone staple mounted thereon in an expanded state or configuration.
Figure 4A:
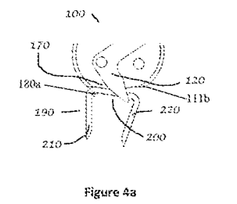
FIG. 4a is a front elevational, magnified view of the distal end of the bone staple insertion tool or instrument or tool of FIG. 1 with a bone staple mounted thereon in the non-expanded or relaxed state or configuration.

Referring to FIGS. 3a and 4a, a bone staple 190 is shown in the non-expanded or relaxed state or configuration, removably mounted onto the distal aspect or distal surface 111 of the first preferred bone staple insertion tool or instrument 100 and positioned such that the approximate mid-point of the bone staple inter-axis 200 is proximate the body fulcrum 170. In this configuration, the sterilized bone staple 190 and sterilized instrument 100 are preferably positioned in the sterilized packaging and may be locked or secured in the non-expanded or relaxed state for shipment and delivery. The bone staple mount 180 is thereby positioned outwardly along the distal aspect of the body 110 such that it engages the bone staple 190 proximate to the intersection of the bone staple inter-axis 200 and a first bone staple leg 210 and maintains the proximal surface of the staple inter-axis 200 proximate to the distal surface 111 of the body 110. The pivot hole 160 of the body 110 is located to effectively position the force applicator staple pin 140 proximate to the intersection of bone staple inter-axis 200 and a second bone staple leg 220. The force applicator 120 is shown in FIG. 3a in a first position at an acute angle of rotation relative to the body 110 such that the bone staple 190 is maintained proximate the distal aspect of the body 110 being engaged by the force applicator staple pin 140, the fulcrum 170, and the mount 180.

In the first preferred embodiment, the bone staple 190 is maintained in a position relative to the bone staple instrument 100 and retains a first shape, i.e., in a non-expanded, relaxed initial state, whereby the staple legs 210, 220 are oriented toward each other in their biased position. It can be appreciated that slight angular positional changes of the force applicator 120 from the first position can increase or decrease the engagement force of the staple pin 140 onto the bone staple 190, thereby increasing or decreasing the reactive forces of the fulcrum 170 and mount 180 such that the bone staple 190 will be maintained in place with greater or lesser security, respectively. In another aspect of the first preferred embodiment, the force applicator 120 is maintained at approximately the first position, i.e., prevented from further rotation in a clockwise direction as viewed in FIG. 3a, thereby maintaining a secured engagement with the bone staple 190 and the insertion instrument body 110 and mount 180, for the purpose of retaining the bone staple 190 in position on the bone staple insertion instrument 100. The means for prohibiting additional clockwise rotation, as viewed in FIG. 3b, of the first applicator 120, which is an arm in the first preferred embodiment, can be achieved using simple mechanical means such as a buttress extending from the body 110, or other features that would be apparent to those skilled in the art based on a review of the present disclosure.

Figure 4B:
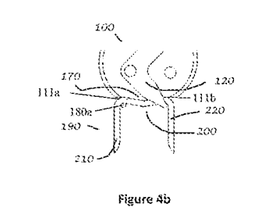
FIG. 4b is a front elevational, magnified view of the distal end of the bone staple insertion instrument or tool of FIG. 1 with a bone staple mounted thereon in the expanded state or configuration.

Referring to FIGS. 3b and 4b, a bone staple 190 is shown in the expanded state or configuration mounted onto the distal aspect or distal surface 111 of the insertion instrument 100 and positioned such that the approximate mid-point of the bone staple inter-axis 200 is proximate the body fulcrum 170. The center portion or mid-point of the bone staple inter-axis 200 is also preferably positioned proximate or on the longitudinal axis 110b, which preferably extends through the fulcrum 170 in the first preferred embodiment. The bone staple mount 180 is engaged with the bone staple 190, maintaining the proximal surface of the inter-axis 200 proximate to the distal aspect or distal surface 111 of the body 110. The force applicator 120 is rotated about the pivot pin 130 from the relaxed configuration as shown in FIG. 3a to the expanded configuration as shown in FIG. 3b in a counter-clockwise direction, whereby the staple pin 140 is pivoted proximally and outwardly from the relaxed configuration to the expanded configuration. The force induced onto the distal surface of the bone staple inter-axis 200 by the force applicator staple pin 140 causes the inter-axis 200 to bend at the fulcrum 170 as the proximal surface of the inter-axis 200 proximate to the staple pin 140 is translated proximally. The bone staple inter-axis 200 is thereby forced into the expanded configuration, wherein the bone staple legs 210, 220 are preferably oriented parallel to each other. The first and second bone staple legs 210, 220 are not limited to being positioned parallel to each other in the expanded configuration and may be positioned slightly beyond parallel outwardly or slightly short of parallel inwardly, as long as the bone staple 190 is moved or expanded from its biased position (FIGS. 3a and 4a) to its expanded position (FIGS. 3b and 4b), wherein the bone staple 190 is biased toward its biased position after insertion and release from the bone staple 100. The first and second legs 210, 220 are preferably positioned relatively parallel to each other in the expanded configuration for substantial straight insertion into the patient during use, thereby limiting insertion forces and lateral reaction forces being induced during insertion.

Figures 5A, 5B:
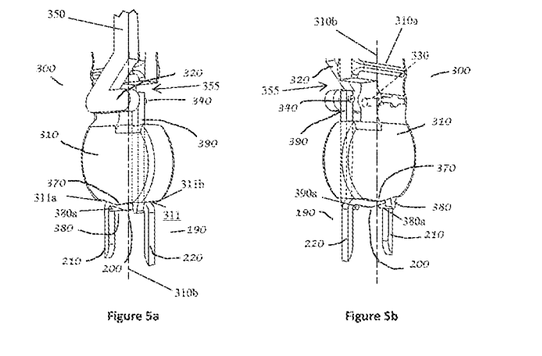
FIG. 5a is a front perspective, magnified view of a distal end of a bone staple insertion instrument or tool in accordance with a second preferred embodiment of the present invention with a bone staple mounted thereto and positioned in an expanded state or configuration.
FIG. 5b is a rear perspective, magnified view of the distal end of the bone staple insertion instrument or tool of FIG. 5a with the bone staple mounted thereto and positioned in the expanded state or configuration.

Referring to FIGS. 5a and 5b, a second preferred embodiment of a bone staple insertion instrument 300 includes a body 310, a force applicator 320, a first bone staple mount 380, and a second elongate staple mount or staple pin portion 390. The body 310 includes a proximal portion 310a, although only a portion is shown in FIGS. 5a and 5b, a distal surface 311 and a fulcrum 370, similar to the first preferred embodiment. The body 310 defines a longitudinal axis 310b and the fulcrum 370 is positioned on the distal surface 311 proximate the longitudinal axis 310b. The distal surface 311 has a first end 311a and a second end 311b. The bone staple mount 380 is fixed to the body 310 and extends from the body 310 proximate the first end 311a with a first pin 380a separated from the distal surface 311 by a space for insertion of the bone staple 190 near an intersection of the inter-axis 200 with the first leg 210. The force applicator 320 is movably attached to the body 310. The force applicator 320 has a gripping portion 350 and the staple pin portion 390 with the second pin 390a on its distal end. The second pin 390a is spaced from the distal surface 311 in an assembled configuration for insertion of the inter-axis between the second pin 390a and the distal surface 311 near an intersection of the inter-axis 200 and the second leg 220. The force applicator 320 is configured to receive the bone staple 190 between staple pin portion 390 and the distal surface 311 and, upon actuation of the gripping portion 350, bends the inter-axis 200 of the bone staple 190 across the fulcrum 370 located between the bone staple mount 380 and the staple pin portion 390 to move the bone staple 190 to the expanded state or configuration. In the expanded configuration, the first and second legs 210, 220 are positioned substantially parallel to each other.

A pivot grip pin 330, shown in dashed line type, which is substantially identical to the pivot pin 130 of the first preferred embodiment, of the force applicator 320 and an associated pivot hole, not shown but substantially identical to the pivot hole 160 shown in the first preferred embodiment, located in the body 310 are incorporated in the second preferred embodiment. The force applicator pivot pin 330 is rotatably engaged in the pivot hole such that the force applicator 320 is able to rotate about the axis of the pivot pin 330 relative to the insertion instrument body 310. The axis of the pivot pin 330 is substantially perpendicular to front and rear faces of the body 310 in the second preferred embodiment. The force applicator 320 includes the proximal gripping portion 350, although only a portion is shown in FIGS. 5a and 5b, but is substantially the same as the gripping portion 150 of the first preferred embodiment, proximal to the pivot pin 330 and a mount pin portion 340 at a radial distance from the pivot pin 330 that is positioned in the pivot hole in the body 310. The mount pin 340 is rotatably engaged with the proximal aspect of the elongated second staple mount or the actuating rod 390, which includes a rod proximal end having a pivot hole, such that rotation of the force applicator 320 about the pivot pin 330 causes the elongated second staple mount or actuating rod 390 to translate generally in a proximal/distal direction or parallel to a longitudinal axis of the body 310. The elongated second staple mount or actuating rod 390 is positioned in a channel in the distal portion of the body 310 to guide the substantially linear translation of the elongated second staple mount 390 relative to the body 310. In the second preferred embodiment, a counter-clockwise rotation, as viewed in FIG. 5a, of the force applicator 320 would cause a generally proximal translation of the second staple mount 390, and likewise a clockwise rotation of the force applicator 320, as viewed in FIG. 5a, would cause a generally distal translation of the elongated staple mount 390. It is contemplated that various other physical arrangements of the force applicator 320 and the pivot pin 330 in relation to the second staple mount 390 would cause proximal translation of the second staple mount 390 with clockwise rotation of the force applicator 320 and vice versa.

Similar to first preferred embodiment described above, a first bone staple mount 380 is fixed at the most distal aspect of body 310 such that the distal end of the first bone staple mount 380 extends from the distal end of the body 310, as shown in FIG. 5a. The bone staple fulcrum 370 is located at the most distal aspect of the body 310 and is preferably centered on the most distal aspect or the distal surface 311, such that the distal surface 311 of the body 310 extending outward in either direction from the fulcrum 370 is proximal to the fulcrum 370 or tapers from the fulcrum 370 toward the proximal end of the body 310. In the second preferred embodiment shown in FIGS. 5a-5b, the distal surface 311 linearly tapers proximally with increasing distance outward from the fulcrum 370, however alternative configurations may utilize other geometries, such as a step or curve. The mount pin portion 340 on the proximal gripping portion 350 that is positioned in the pivot hole in the second elongate staple mount or the actuating rod 390 is positioned in a cutout 355 in the body 310.

The bone staple 190 is shown removably mounted onto the distal aspect or distal surface 311 of the insertion instrument 300 of the second preferred embodiment and positioned such that the approximate mid-point of the bone staple inter-axis 200 is proximate the body fulcrum 370 in FIGS. 5a and 5b. The bone staple mount 380 is thereby positioned outwardly along the distal aspect of the body 310 such that it engages the bone staple 190 proximate to the intersection of the bone staple inter-axis 200 and the first bone staple leg 210 and maintains the proximal surface of the staple inter-axis 200 proximate to the distal surface 311 of the body 310.

The second staple mount 390 includes a distal bone staple engaging portion or second pin 390a, similar or substantially the same as the pin 140 of the first preferred embodiment, and is slidably engaged to the distal aspect or distal surface 311 of the body 310 of the insertion instrument 300. The second staple mount or actuating rod 390 is positioned opposite the fulcrum 370 at approximately the same distance from the fulcrum 370 as the first staple mount 380 in the mounted configuration. In the second preferred embodiment, the second staple mount or actuating rod 390 is positioned within an elongate opening of the distal aspect of the body 310 such that translation in an approximate proximal/distal direction is enabled and guided by the elongate opening. It can be conceived that other arrangements and configurations for slidably engaging the second staple mount or actuating rod 390 in the body 310 such that the translational motion is maintained, such as a groove, slot, or other accommodating opening may be constructed without significantly impacting the function or operation of the instrument 300. As described in the first preferred embodiment but not shown for the second preferred embodiment, the force applicator 320 is placed in a first position such that the distal aspect of the second staple mount 390 is maintained proximate the distal aspect of the body 310 as to engage the bone staple 190 whereby the bone staple 190 can be secured to the insertion instrument 300.

The force applicator 320 is rotated about the pivot pin in a counter-clockwise direction in FIG. 5*a*, from a first position, not shown but similar to the position of the force applicator 120 proximal portion 150 of the first preferred embodiment such that the bone staple 190 is retained and in a relaxed, i.e., non-expanded, state, to a second position as shown in FIG. 5*a*, whereby the second staple mount 390 is translated generally proximally from a first or non-expanded position to a second position or expanded position. The force thereby induced onto the distal surface of the bone staple inter-axis 200 by the second staple mount 390 causes the inter-axis 200 to bend at the fulcrum 370 as the inter-axis 200 proximate to the engagement location of the second staple mount 390 is translated proximally. The bone staple inter-axis 200 is thereby forced into the second, i.e., expanded configuration or shape whereby the first and second bone staple legs 210, 220 are oriented parallel to each other or substantially parallel to each other for insertion or implantation into the patient. Following insertion into the patient, preferably into bone segments, the bone staple 190 is released from the bone staple instrument 300 and the first and second legs 210, 220 apply an inward force toward each other to urge the bone segments toward each other to promote fusion of the bone segments or to secure the bone staple 190 and engaged soft tissue to the bone. The body 310 may also be utilized to further urge the bone staple 190 into the patient following release of the bone staple from the body 310.

Figure 6:
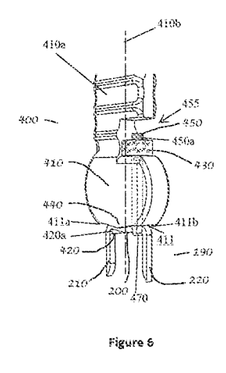
FIG. 6 is a front perspective, magnified view of a distal end of a bone staple insertion instrument or tool in accordance with a third preferred embodiment of the present invention with a bone staple mounted thereto and positioned in an expanded state or configuration.

A third preferred embodiment, as shown in FIG. 6, describes an insertion instrument 400 similar to the first and second preferred embodiments previously described and presented in FIGS. 2-5*b*. However, the third preferred embodiment of the bone staple insertion instrument 400 differs in that the force applicator 430 acting on the second staple mount 450 is not a pivotable elongate member with a proximal gripping portion extending along the body 410, a pivot pin, and mount pin, but rather a threaded member or force applicator 430 depicted as a nut. The second staple mount 450 of the third preferred embodiment is an elongate member with a distal end configured as the staple pin portion 470 for engaging the bone staple 190 and slidably mounted on the distal aspect of body 410, as was described in the second preferred embodiment, and a proximal end with external threads 450*a* for engaging the force applicator 430, which is comprised of the nut in the third preferred embodiment. The force applicator 430, its distal surface in abutment with the body 410, is rotated about its central axis in a clockwise direction, translating the second staple mount 450 from a first position or non-expanded configuration, not shown but similar to the previous first and second preferred embodiments, such that the bone staple 190 is retained and in a relaxed, i.e., non-expanded, state, to a second position or expanded configuration, as shown in FIG. 6, whereby the second staple mount 450 is translated generally proximally from the first non-expanded position to the second expanded position. The force thereby induced onto the distal surface of the bone staple inter-axis 200 by the second staple mount 450 causes the inter-axis 200 to bend at the fulcrum 440 as the inter-axis 200 proximate to the engagement location of the second staple mount 450 is translated proximally. The bone staple inter-axis 200 is thereby forced into the second, i.e., expanded shape or configuration, whereby the first and second bone staple legs 210, 220 are oriented substantially parallel to each other for insertion or implantation into the patient.

The bone staple insertion instrument or tool 400 of the third preferred embodiment also includes a bone staple mount or first mount 420 fixedly attached to the body 410 proximate the first end 411*a* of the distal surface 411. The first mount 420 includes a first pin 420*a* extending from a distal end that is spaced from the body 410 approximately the thickness of or slightly larger than the thickness of the inter-axis 200 of the bone staple 190 for insertion of the inter-axis 200 therein. The staple pin portion 470 also includes the second pin that is spaced from the distal surface 411 for insertion of the inter-axis 200 therein near the intersection of the second leg 220 and the inter-axis. The body 410 includes the proximal portion 410*a* and defines the longitudinal axis 410*b*. The force applicator 430 with the second staple mount 450 is configured to receive the bone staple 190 between the staple pin portion or second pin and the distal surface 411 and, upon actuation of the force applicator or gripping portion 430, bend the inter-axis 200 of the bone staple 190 across the fulcrum 440 located between the bone staple mount 420 and the pin of the second staple mount 450 to move the bone staple 190 to an expanded state or configuration (FIG. 6) wherein the first and second legs 210, 220 are positioned substantially parallel to the longitudinal axis 410*b*.

Figure 7:
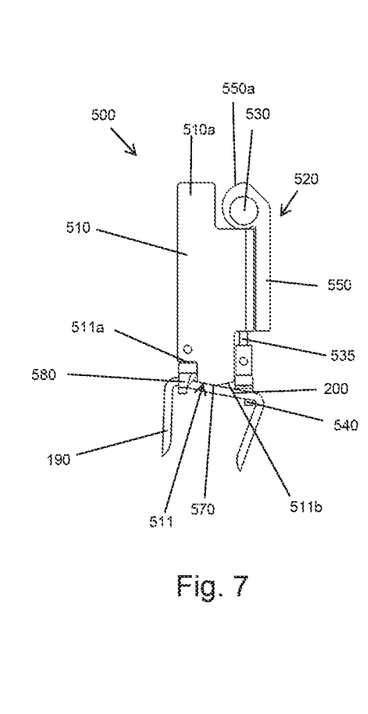
FIG. 7 is a front perspective view of a bone staple insertion tool or instrument in accordance with a fourth preferred embodiment of the present invention, with a bone staple mounted thereon in a non-expanded or relaxed state or configuration.
Figure 8:
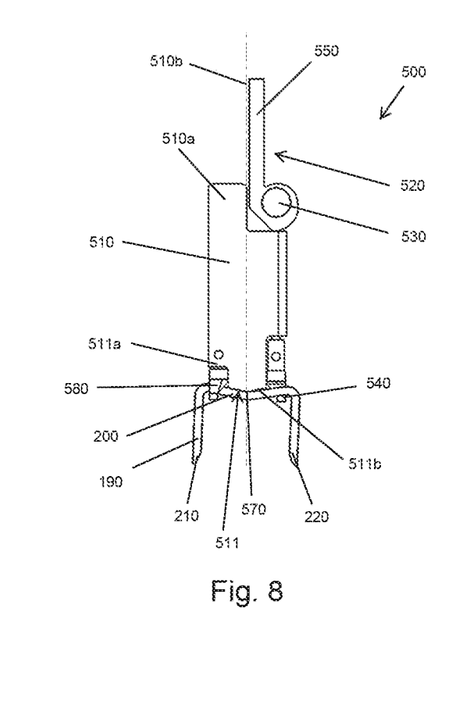
FIG. 8 is a front perspective view of the bone staple insertion tool or instrument of FIG. 7 with a bone staple mounted thereon in an expanded state or configuration.
Figure 9:
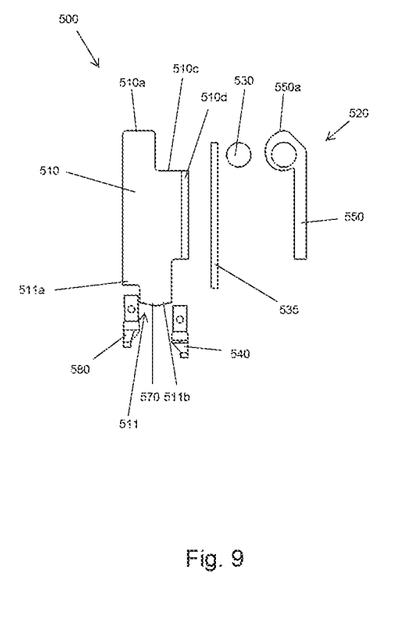
FIG. 9 is an exploded view of the bone staple insertion tool or instrument of FIG. 7.

Referring to FIGS. 7-9, a fourth preferred embodiment of the preferred bone staple insertion instrument or tool 500 has similarities to the first, second and third preferred bone staple insertion tools 100, 300, 400 and like numerals are generally utilized to identify like features, with a "5" prefix to distinguish the fourth preferred bone staple insertion instrument or tool 500. The fourth preferred embodiment of the bone staple insertion instrument or tool 500 includes a body 510, a force applicator 520, a bone staple mount 580 that is substantially fixed to the body 510, and a bone staple fulcrum 570 at the distal aspect or distal surface 511 of the body 510. The force applicator 520 preferably has a gripping portion 550 that is pivotable relative to the body 510 and rotates about a pivot pin 530 to actuate a staple pin portion 540 extending from the body 510. The bone staple mount 580 and the staple pin portion 540 are preferably generally L-shaped such that the bone staple 190 may slide on to or off of the bone staple mount 580 and the staple pin portion 540 in only one direction. More preferably, the L-shaped nature of the bone staple mount 580 and the staple pin portion 540 are oriented in opposing directions such that the bone staple 190 is mounted or dismounted from the tool 500 by rotating the tool 500.

The body 510 of the fourth preferred embodiment includes a proximal portion 510*a* and defines a longitudinal axis 510*b*. The fulcrum 570 is preferably positioned on the distal surface 511 on the longitudinal axis 510*b*. The distal surface 511 preferably includes a first end 511*a* and a second end 511*b*. A bone staple mount 580 is fixed to the body 510 and extends from the body 510 proximate the first end 511*a*. The force applicator 520 is movably attached to the body 510 and preferably includes the gripping portion 550, the pivot pin 530, the actuating rod 535 and the staple pin portion 540. In the fourth preferred embodiment, the actuating rod 535 is threaded on both ends to threadably engage the pivot pin 530 at the proximal end and the staple pin portion 540 at the distal end. The threaded engagement also aids in both assembly of the insertion instrument or tool 500 and adjustment of the staple pin portion 540 relative to the staple mount 580 and fulcrum 570 so that it may be positioned optimally for securing the bone staple 190 to the distal surface 511 in preparation for shipping and storage in an unexpanded state. The actuating rod 535 is not so limited and may be otherwise designed and configured to take on the general shape of the actuating rod 535, withstand the normal operating conditions of the actuating rod 535 and perform the preferred functions of the actuating rod 535. For example, the actuating rod 535 may be integrally formed with the staple pin portion 540 and/or the pivot pin 530, may be comprised of a wire (not shown) attached to the staple in portion 540 that wraps around the pivot pin 530 when actuated to draw the staple pin portion 540 toward the distal surface 511 or may be otherwise designed and configured. The actuating rod 535 may alternatively be comprised of an elongate actuating rod with a pivot hole on a proximal end that receives the pivot pin 530. The staple pin portion 540 is movably positioned proximate the second end 511b. The force applicator 520 is configured to receive the bone staple 190 between the staple pin portion 540 and the distal surface 511 and, upon actuation of the gripping portion 550, bend the inter-axis 200 of the bone staple 190 across the fulcrum 570 located between the bone staple mount 580 and the staple pin portion 540 to move the bone staple 190 to an expanded state or configuration (FIG. 8). In the expanded configuration, the first and second legs 210, 220 are positioned substantially parallel to each other and to the longitudinal axis 510b.

Referring to FIG. 7, a bone staple 190 is shown mounted to the fourth preferred embodiment of the bone staple insertion instrument 500 in a relaxed, non-expanded state, wherein the first and second bone staple legs 210, 220 are oriented toward each other as they extend from the inter-axis 200 of the bone staple 190. The bone staple insertion instrument 500 with the bone staple 190 mounted thereto in the non-expanded configuration is preferably positioned in a sterilized package for shipping and delivery to the user. The insertion instrument 500 has a relatively low profile with the gripping portion 550 positioned against the body 510. The inter-axis 200 of the bone staple 190 is shown mounted to the bone staple mount 580 and the staple pin portion 540 at or near each end of the inter-axis 200, with the approximate center of the inter-axis 200 abutting the fulcrum 570. The fourth preferred embodiment may be provided in nearly any size such that the bone staple mount 580 and staple pin portion 540 are appropriately spaced to accommodate any size bone staple 190. Preferably, the bone staple 190 may range from eight to twenty five millimeters (8-25 mm) along the inter-axis 200, while the first and second legs 210, 220 of the bone staple 190 may range from eight to twenty millimeters (8-20 mm) in length. The first and second legs 210, 220 may also be barbed, smooth, or any other suitable shape for engaging and being inserted into the patient, preferably into bone segments.

To use the bone staple insertion tool 500 of the fourth preferred embodiment, a user removes the tool 500 and bone staple 190 from the sterilized package and actuates the force applicator 520 by rotating the gripping portion 550 away from the body 510, which causes the staple pin 540 to retract toward the body 510, in turn causing the inter-axis 200 to bend around the fulcrum 570, thereby resulting in the bone staple 190 being in the expanded state shown in FIG. 8. In the expanded state or configuration, the first and second bone staple legs 210, 220 are generally parallel to each other. The rotation of the gripping portion 550 preferably causes the staple pin 540 to retract through a cam action, but is not so limited. A user may then insert the bone staple 190 into a patient as described above, de-actuate the gripping portion 550 of the force applicator 520 to release any force placed on the bone staple 190 by the insertion tool 500 and then rotate the insertion tool 500 such that the bone staple mount 580 and staple pin portion 540 may freely rotate from engagement with the bone staple 190. The user may then utilize the body 510 to urge the bone staple 190 further into the bone segments, such as by tamping on the bone staple 190

In the fourth preferred embodiment, the gripping portion 550 of the force applicator 520 extends from the body 510 and rotates radially about the pivot pin 530. Rotation of the gripping portion 550 from an initial position (FIG. 7) against the body 510 to an actuated position (FIG. 8) spaced from the body 510 and preferably extending upwardly, substantially parallel to the longitudinal axis 510b, causes the staple pin portion 540 and associated second pin to retract toward the body 510 through a cam action. In the fourth preferred embodiment, the staple pin portion 540 is threadably attached to the actuating rod 535, which is threadably attached to the pivot pin 530. The actuating rod 535 is positioned in a channel in the body 510 and extends substantially parallel to the longitudinal axis 510b. The actuating rod 535 includes a rod proximal end 535a having threads that engage a threaded hole in the pivot pin 530. The preferred force applicator 520 includes the pivot grip pin 530 that is separate from the gripping portion 550 and the actuating rod 535, but is not so limited and the pivot grip pin 530 may be integrally formed on the gripping portion 550 or the actuating rod 535, without significantly impacting the function or operation of the bone staple insertion instrument 500. The gripping portion 550 also includes a first cam surface 550a positioned proximate the pivot grip pin 530. The body 510 includes a second cam surface 510c and the first cam surface 550a is in engagement with the second cam surface 510c in an assembled configuration. The engagement of the first cam surface 550a with the second cam surface 510c coupled with pivoting of the gripping portion 550 relative to the body 510 causes the force applicator 520 to actuate movement of the actuating rod 535 and the staple pin portion 540. The body 510 of the fourth preferred embodiment also includes a grip slot 510d at a proximal portion of the body 510 on a side of the body 510 proximate the second end 511b. The gripping portion 550 is positioned in the grip slot 510d when the insertion tool or instrument 500 is in the non-expanded configuration (FIG. 7) and extends away from the body 510 spaced from the grip slot 510d when the insertion tool 500 is in the expanded state or configuration (FIG. 8).

In operation, the bone staple insertion instrument 500 is preferably supplied to a user in a sterilized package in the non-expanded configuration (FIG. 7). The user may drill pilot holes in adjacent bone segments at the spacing of the first and second bone staple legs 210, 220 and the bone staple insertion instrument 500 is removed from the packaging. The user grasps the gripping portion and pivots the gripping portion 550 such that the instrument 500 is in the expanded configuration (FIG. 8). In the expanded configuration, the gripping portion 550 extends away from the body 510 with the handle substantially parallel to the longitudinal axis 510b and the first cam surface 550a cooperates with the second cam surface 510c to urge the actuating rod 535 and the staple pin portion 540 toward the proximal end. In the expanded configuration, the hook on the staple pin portion 540 bends the inter-axis 200 over the fulcrum 570 such that the first and second legs 210, 220 are substantially parallel to each other. The user then inserts the first and second legs 210, 220 into the pilot holes in the bone segments and the gripping portion 550 is pivoted back into the grip slot 510d such that the staple pin portion 540 is released from the inter-axis 200. The user is then readily able to pivot the body 510 relative to the inserted staple 190 to release the body 510 from the staple 190. The inter-axis 200 is preferably relatively close to the patient's soft tissue and bone such that the staple 190 has a relatively low profile after insertion. The preferred shape-memory properties of the material of the staple 190, such as Nitinol, causes the staple 190 to apply a compression force on the bone segments as the legs 210, 220 attempt to or are biased to move toward each other.

It is contemplated that the force applicator 120, 320, 450, 520 of any of the preferred embodiments may be constructed in a number of various mechanical actuator designs capable of acting on the second staple mount 390, 450 or staple pin portion 140, 540 to apply a directional force whereby the second staple mount 390, 450 translates or the staple pin portion 140, 540 pivots or translates in a generally proximal/distal direction and acts forcibly on the bone staple 190 to retain and secure the bone staple 190 on the insertion instrument body 110, 310, 410, 510 and expands the staple 190 to the expanded state where the first and second staple legs 210, 220 are generally parallel for insertion into the patient. Various mechanical levers, cams, slides, etc. are capable of driving the second staple mount 390, 450 or the staple pin portion 140 in a general proximal/distal direction, thereby achieving the fixation and manipulation of the bone staple 190 by the insertion instrument 100, 300, 400, 500, as described herein.

It should be understood that while the preferred embodiments disclosed herein have demonstrated an engagement with the surgical bone staple 190, the insertion instruments 100, 300, 400, 500 are not to be limited to securing, forcibly manipulating, and inserting the bone staples 190 alone. These preferred embodiments may be used in various ways other than those described herein, such as by way of non-limiting example, bending a bone fixation plate, securing a K-Wire, or interlocking components of a total joint whereby proper alignment and force is required or desired. Further, it is contemplated that the preferred insertion instruments 100, 300, 400, 500 may be packaged into terminally sterilized packaging alone, with an appropriately sized bone staple 190 removably mounted thereon, or in combination with other surgical tools and implants such as, by way of non-limiting example, drill bits, sizing templates, locator pins, tamps, bone plates, bone screws, and the like. Accordingly, the preferred embodiments of the insertion instruments 100, 300, 400, 500 may comprise rigid and preferably biocompatible materials, including metal, polymeric, plastic, or a combination thereof.

In operation, the bone staple 190 is inserted into a patient with the bone staple insertion tool 100, 300, 400, 500 by mounting the bone staple 190 to the bone staple insertion tool 100, 300, 400, 500 with the inter-axis 200 of the bone staple 190 engaged by the gripping portion or bone staple mount 180, 380, 420, 580 and the staple pin portion or staple mount 140, 390, 450, 540 with a central portion of the inter-axis 200 positioned on the fulcrum 170, 370, 440, 570. The force applicator 120, 320, 430, 520 is actuated to cause the staple pin portion or staple mount 140, 390, 450, 540 to bend the inter-axis 200 across the fulcrum 170, 370, 440, 570 such that first and second legs 210, 220 of the bone staple 190 are substantially parallel to each other. The bone staple 190 is then inserted into the patient, preferably into two separated bone segments and the force applicator 120, 320, 430, 520 is de-actuated. The bone staple insertion tool or instrument 100, 300, 400, 500 is then rotated to release the bone staple 190 from the tool 100, 300, 400, 500. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the appended claims.

I claim:

1. A bone staple insertion tool for inserting a bone staple having an inter-axis and first and second legs into a patient, the insertion tool comprising:
   a body having a proximal portion, a distal surface and a fulcrum, the body defining a longitudinal axis and the fulcrum positioned on the distal surface proximate the longitudinal axis, the distal surface having a first end and a second end;
   a bone staple mount fixed to the body and extending from the body proximate the first end; and
   a force applicator movably attached to the body, the force applicator having a gripping portion and a staple pin portion, the staple pin portion positioned proximate the second end, the force applicator configured to receive the bone staple between the staple pin portion and the distal surface and, upon actuation of the gripping portion, bend the inter-axis of the bone staple across the fulcrum located between the bone staple mount and the staple pin portion to move the bone staple to an expanded state, wherein the first and second legs are positioned substantially parallel to the longitudinal axis.

2. The bone staple insertion tool of claim 1, wherein the gripping portion of the force applicator extends from the body and rotates radially about a pivot pin.

3. The bone staple insertion tool of claim 2, wherein rotation of the gripping portion causes the staple pin portion to retract toward the body through a cam action.

4. The bone staple insertion tool of claim 1, wherein the bone staple mount and the staple pin portion of the force applicator are substantially L-shaped.

5. The bone staple insertion tool of claim 4, wherein the bone staple mount and the staple pin portion of the force applicator are oriented in generally opposing directions.

6. The bone staple insertion tool of claim 1, wherein the force applicator is further configured to release the bone staple upon a de-actuation of the gripping portion.

7. The bone staple insertion tool of claim 1, wherein the distal surface tapers proximally from the fulcrum toward the first end and the second end.

8. The bone staple insertion tool of claim 1, wherein the force applicator includes a first cam surface and the body has a second cam surface, the first cam surface in facing engagement with the second cam surface.

9. The bone staple insertion tool of claim 1, wherein the distance between the fulcrum and the bone staple mount is approximately equal to the distance between the fulcrum and the staple pin portion.

10. The bone staple insertion tool of claim 1, the distance between the fulcrum and the bone staple mount is less than the distance between the fulcrum and the staple pin portion.

11. The bone staple insertion tool of claim 1, wherein the staple pin portion is attached to an actuating rod, the actuating rod positioned in a channel in the body, the channel extending substantially parallel to the longitudinal axis, the channel including a channel proximal end having a pivot hole.

12. The bone staple insertion tool of claim 11, wherein the force applicator includes a pivot grip pin on the gripping portion rotatably positioned in the pivot hole, the gripping portion including a first cam surface positioned proximate the pivot pin.

13. The bone staple insertion tool of claim 12, wherein the body includes a second cam surface, the first cam surface in engagement with the second cam surface in an assembled configuration and configured to actuate the force applicator as the gripping portion is pivoted about the pivot hole on the grip pin.

14. The bone staple insertion tool of claim 12, wherein the actuating rod is threadably engaged to the staple pin portion and threadably engaged to the pivot grip pin.

15. The bone staple insertion tool of claim 1, wherein the gripping portion of the force applicator is pivotable relative to the body.

16. The bone staple insertion tool of claim 15, wherein the body includes a grip slot, the gripping portion positioned in the grip slot when the insertion tool is in a non-expanded configuration, the gripping portion extending away from the body spaced from the grip slot when the insertion tool is in the expanded state.

17. The bone staple insertion tool of claim 1, wherein the force applicator includes a mount pin portion on the gripping portion and a second elongate staple mount, the staple pin portion attached to the second elongate staple mount.

18. The bone staple insertion tool of claim 17, wherein the body includes a cutout, the staple pin portion positioned in the cutout.

19. A method of inserting a bone staple into a patient with a bone staple insertion tool having a body with a fulcrum on a distal surface, a bone staple mount and a force applicator having a gripping portion and a staple pin portion, the fulcrum positioned on the distal surface between the bone staple mount and the staple pin portion, the method comprising the steps of:
   mounting the bone staple to a bone staple insertion tool with an inter-axis of the bone staple engaged by the bone staple mount and the staple pin portion with a central portion of the inter-axis positioned on the fulcrum;
   actuating the gripping portion to cause the staple pin portion to bend the inter-axis across the fulcrum such that first and second legs of the bone staple are substantially parallel to each other;
   inserting the bone staple into the patient;
   de-actuating the gripping portion; and
   sliding the bone staple insertion tool off of the bone staple to release the bone staple from the bone staple insertion tool.

20. The method of claim 19, wherein actuating the gripping portion causes the gripping portion to rotate about a pivot pin.

21. The method of claim 20, wherein actuating the gripping portion causes the staple pin portion to translate substantially linearly relative to the body.

22. The method of claim 21, wherein actuating the gripping portion causes the force applicator to both pivot and translate substantially linearly relative to the body.

23. The method of claim 19, wherein the bone staple insertion tool is rotated relative to the bone staple to release the bone staple insertion tool from the bone staple.

24. The method of claim 19, wherein the bone staple mount and the staple pin portion slide off of the inter-axis to release the bone staple from the bone staple insertion tool.

* * * * *